US 6,503,919 B1

(12) United States Patent
Koch et al.

(10) Patent No.: US 6,503,919 B1
(45) Date of Patent: *Jan. 7, 2003

(54) COMPOUNDS OF 7-OXO-2,3,7,14-TETRAHYDRO-1H-BENZO[B]PYRANO[3,2-H] ACRIDIN CARBOXYLATE

(75) Inventors: Michel Koch, La Celle Saint Cloud (FR); François Tillequin, Paris (FR); Sylvie Michel, Paris (FR); Ghanem Atassi, Saint Cloud (FR); Alain Pierre, Les Alluets le Roi (FR); Pierre Renard, Le Chesnay (FR); Bruno Pfeiffer, Saint Leu la Foret (FR)

(73) Assignee: Les Laboratoires Server, Neuilly sur Seine (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/594,853

(22) Filed: Jun. 15, 2000

(30) Foreign Application Priority Data

Jun. 16, 1999 (FR) .............................. 99 07611

(51) Int. Cl.[7] ............... C07D 491/052; C07D 491/153; A61K 31/4741
(52) U.S. Cl. ............... 514/279; 514/211.09; 514/230.8; 514/232.8; 514/279; 514/280; 546/41; 546/47
(58) Field of Search .................. 546/41, 47; 514/279, 514/280

(56) References Cited

U.S. PATENT DOCUMENTS 6,288,073 B1 * 9/2001 Koch et al. ................ 514/279

* cited by examiner

Primary Examiner—Alan L. Rotman
Assistant Examiner—Janet L Coppins
(74) Attorney, Agent, or Firm—The Firm of Hueschen and Sage

(57) ABSTRACT

A compound selected from those of formula (I):

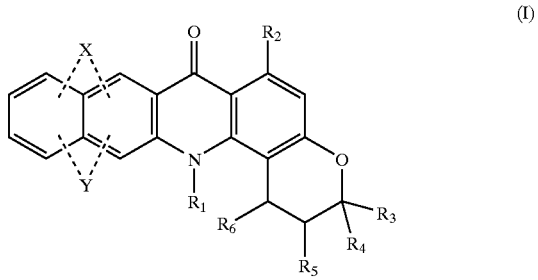

wherein:

X and Y represent hydrogen, halogen, hydroxy, mercapto, cyano, nitro, alkyl, alkoxy, trihaloalkyl, optionally substituted amino, methylenedioxy, or ethylenedioxy, $R_1$ represents hydrogen, or alkyl, $R_2$ represents hydrogen, hydroxy, alkyl, alkoxy, alkylcarbonyloxy, or optionally substituted amino, $R_3$ and $R_4$ represent hydrogen, or alkyl, $R_5$ and $R_6$ represent —O—CO—U—V wherein U and V are as defined in the description, or Z as defined in the description, it being understood that at least one of the $R_5$ and $R_6$ groups represents —O—CO—U—V, their isomers, N-oxides, and pharmaceutically-acceptable acid or base addition salts thereof, and medicinal products containing the same which are useful in the treatment of cancer.

12 Claims, No Drawings

COMPOUNDS OF 7-OXO-2,3,7,14-TETRAHYDRO-1H-BENZO[B]PYRANO[3,2-H] ACRIDIN CARBOXYLATE

FIELD OF THE INVENTION

The present invention relates to new compounds of 7-oxo-2,3,7,14-tetrahydro-1H-benzo[b]pyrano[3,2-h]acridin carboxylate and to pharmaceutical compositions containing them.

The compounds of the invention are derivatives of acronycine which is an alkaloid having anti-tumour properties that have been demonstrated in experimental models (*J. Pharm. Sci.* 1966, 55 (8), 758–768). Despite a broad spectrum of activity, however, acronycine is sparingly soluble, which limits its bioavailability and its use in pharmaceutical compositions for administration by injection.

Various modifications have been made to this molecule, such as those described in *J. Med. Chem.,* 1996, 39, 4762–4766, and have made it possible to resolve some of the difficulties associated with the problem of the solubility of these compounds. Nevertheless, anti-cancer therapy requirements call for the constant development of new anti-tumour agents with the aim of obtaining medicaments that are simultaneously more active and better tolerated. In particular, solid tumours pose a major problem in anti-cancer chemotherapy owing to their intrinsic and/or acquired resistance to existing products.

In addition to the fact that the compounds of the invention are new, they have a surprising in vivo and in vitro activity that is superior to that observed hitherto. Moreover, the compounds have valuable properties in respect of solubility, making them suitable for administration of the compounds in liquid form. The compounds discovered by the Applicant thus have anti-tumour properties that make them especially useful in the treatment of cancer, especially of solid tumours.

DETAILED DESCRIPTION OF THE INVENTION

More especially, the present invention relates to compounds of formula (I):

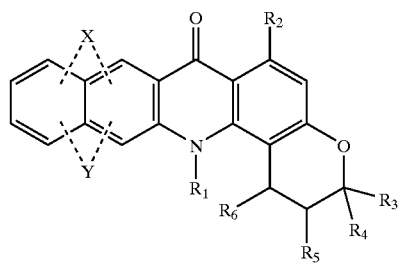

(I)

wherein:
X and Y, which may be identical or different, each independently of the other represents a group selected from a hydrogen atom, a halogen atom, a hydroxy group, a mercapto group, a cyano group, a nitro group, a linear or branched ($C_1$–$C_6$)alkyl group, a linear or branched ($C_1$–$C_6$)alkoxy group, a trihalo-($C_1$–$C_6$)alkyl group in which the alkyl moiety is linear or branched, and an amino group (optionally substituted by one or two identical or different linear or branched ($C_1$–$C_6$) alkyl groups which may themselves be substituted by a linear or branched ($C_1$–$C_6$)alkoxy group or by a group of formula —$NR_7R_8$ wherein $R_7$ and $R_8$, which may be identical or different, each independently of the other represents a hydrogen atom, a linear or branched ($C_1$–$C_6$)alkyl group, an aryl group or an aryl-($C_1$–$C_6$) alkyl group in which the alkyl moiety is linear or branched), or X and Y together form a methylenedioxy or ethylenedioxy group, it being understood that the substituents X and Y may be present on one or the other of the two adjacent benzene rings, $R_1$ represents a hydrogen atom or a linear or branched ($C_1$–$C_6$)alkyl group, $R_2$ represents:
  a hydrogen atom,
  a hydroxy group,
  a linear or branched ($C_1$–$C_6$)alkyl group,
  a linear or branched ($C_1$–$C_6$)alkoxy group optionally substituted by a group selected from:
    a group of formula $NR_9R_{10}$ wherein $R_9$ and $R_{10}$, which may be identical or different, each independently of the other represents a hydrogen atom, a linear or branched ($C_1$–$C_6$)alkyl group, or a linear or branched ($C_1$–$C_6$)hydroxyalkyl group, and
    a saturated or unsaturated monocyclic or bicyclic heterocycle having from 5 to 7 ring members containing one or two hetero atoms selected from oxygen, nitrogen and sulphur,
  a linear or branched ($C_1$–$C_6$)alkylcarbonyloxy group, or
  an amino group optionally substituted by:
    one or two, identical or different, linear or branched ($C_1$–$C_6$)alkyl groups, aryl groups or aryl-($C_1$–$C_6$) alkyl groups in which the alkyl moiety is linear or branched,
    a linear or branched ($C_1$–$C_6$)alkylcarbonyl group optionally substituted by a group —$NR_7R_8$ wherein $R_7$ and $R_8$ are as defined hereinbefore,
    a group of formula —$R_{11}$—$NR_9R_{10}$, wherein $R_{11}$ represents a linear or branched ($C_1$–$C_6$)alkylene group, and $R_9$ and $R_{10}$, which may be identical or different, each independently of the other represents a hydrogen atom, a linear or branched ($C_1$–$C_6$)alkyl group, or a linear or branched ($C_1$–$C_6$)hydroxyalkyl group,
    a linear or branched ($C_1$–$C_6$)alkylene group, substituted by a saturated or unsaturated, monocyclic or bicyclic heterocycle having from 5 to 7 ring members containing one or two hetero atoms selected from oxygen, nitrogen and sulphur, or
    by a group of formula —$R_{11}$—CO—$R_{12}$ wherein $R_{11}$, is as defined hereinbefore, and $R_{12}$ represents a hydroxy group or a linear or branched ($C_1$–$C_6$) alkoxy group, $R_3$ and $R_4$, which may be identical or different, each independently of the other represents a hydrogen atom or a linear or branched ($C_1$–$C_6$)alkyl group, $R_5$ and/or $R_6$ represent(s) a group of formula —O—CO—U—V wherein:
U represents a linear or branched ($C_1$–$C_8$)alkylene chain, optionally substituted by one or more identical or different groups selected from aryl, hydroxy and linear or branched ($C_1$–$C_6$)alkoxy,
V represents a group selected from:
  carboxy, —CO$_2$R$_{13}$ wherein R$_{13}$ represents a linear or branched (C$_1$–C$_6$)alkyl group (optionally substituted by one or more hydroxy groups), an aryl group or an aryl-(C$_1$–C$_6$)alkyl group in which the alkyl moiety is linear or branched,
hydroxy,
linear or branched (C$_1$–C$_6$)alkoxy,
—NR$_7$R$_8$ wherein R$_7$ and R$_8$, which may be identical or different, are as defined hereinbefore,
—NR$_7$—CO$_2$R$_{13}$ wherein R$_7$ and R$_{13}$ are as defined hereinbefore,
—NR$_7$—COR$_{13}$ wherein R$_7$ and R$_{13}$ are as defined hereinbefore,
—COR$_{13}$ wherein R$_{13}$ is as defined hereinbefore, and
—CO—NR$_7$R$_8$ wherein R$_7$ and R$_8$, which may be identical or different, are as defined hereinbefore,
and when only one of the two groups R$_5$ and R$_6$ represents a group of formula —O—CO—U—V, then the other of the said R$_5$ and R$_6$ groups represents a group Z selected from:
hydroxy,
linear or branched (C$_1$–C$_6$)alkoxy,
linear or branched (C$_1$–C$_6$)alkylcarbonyloxy,
arylcarbonyloxy,
aryl-(C$_1$–C$_6$)alkylcarbonyloxy in which the alkyl moiety is linear or branched, and
amino optionally substituted by one or two identical or different linear or branched (C$_1$–C$_6$)alkyl groups,
their isomers, N-oxides, and addition salts thereof with a pharmaceutically acceptable acid or base.

"Aryl" is understood to mean a phenyl or naphthyl group, optionally containing one or more identical or different substituents selected from hydroxy, halogen, carboxy, nitro, amino, (C$_1$–C$_6$)alkylamino or di-(C$_1$–C$_6$)alkylamino in which the(each) alkyl moiety is linear or branched, linear or branched (C$_1$–C$_6$)alkoxy, linear or branched (C$_1$–C$_6$)acyl, and linear or branched (C$_1$–C$_6$)alkylcarbonyloxy.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, lysine, etc.

Among the pharmaceutically acceptable bases there may be mentioned by way of non-limiting example sodium hydroxide, potassium hydroxide, triethylamine, tert-butylamine, etc.

The preferred R$_3$ and R$_4$ substituents according to the invention are linear or branched (C$_1$–C$_6$)alkyl groups in which R$_3$ and R$_4$ may be identical or different. R$_3$ and R$_4$ are preferably identical and each represents a methyl group.

The preferred R$_2$ substituents according to the invention are linear or branched (C$_1$–C$_6$)alkoxy groups, or amino groups optionally substituted by one or two substituents as defined for formula (I).

According to an advantageous embodiment, the preferred compounds of the invention are those wherein R$_5$ represents a group of formula —O—CO—U—V wherein U and V are as defined for formula (I), and R$_6$ represents a group Z as defined for formula (I).

According to another advantageous embodiment, the preferred compounds of the invention are those wherein R$_6$ and R$_5$ each represents an identical group of formula —O—CO—U—V wherein U and V are as defined for formula (I).

The preferred R$_5$ substituent according to the invention is the group of formula —O—CO—U—V wherein U represents a linear (C$_1$–C$_4$)alkylene chain and V represents a group selected from carboxy, —NR$_7$R$_8$, —NR$_7$—CO$_2$R$_{13}$ and —NR$_7$—COR$_{13}$ wherein R$_7$, R$_8$ and R$_{13}$, which may be identical or different, represent a hydrogen atom or a linear or branched (C$_1$–C$_4$)alkyl group.

The preferred R$_6$ substituent according to the invention is the linear or branched (C$_1$–C$_6$)alkylcarbonyloxy group.

The preferred compounds of the invention are:

(±)-cis-4-{[1-(acetyloxy)-6-methoxy-3,3,14-trimethyl-7-oxo-2,3,7,14-tetrahydro-1H-benzo[b]pyrano[3,2-h]acridin-2-yl]oxy}-4-oxobutanoic acid,
(±)-cis-4-({1-[(3-carboxypropanoyl)oxy]-6-methoxy-3,3,14-trimethyl-7-oxo-2,3,7,14-tetrahydro-1H-benzo[b]pyrano[3,2-h]acridin-2-yl}oxy)-4-oxobutanoic acid,
(±)-cis-5-{[1-(acetyloxy)-6-methoxy-3,3,14-trimethyl-7-oxo-2,3,7,14-tetrahydro-1H-benzo[b]pyrano[3,2-h]acridin-2-yl]oxy}-5-oxopentanoic acid,
cis-[1-(acetyloxy)-6-methoxy-3,3,14-trimethyl-7-oxo-2,3,7,14-tetrahydro-1H-benzo[b]pyrano[3,2-h]acridin-2-yl](dimethylamino)acetate, and
cis-[1-(acetyloxy)-6-methoxy-3,3,14-trimethyl-7-oxo-2,3,7,14-tetrahydro-1H-benzo[b]pyrano[3,2-h]acridin-2-yl]4-(dimethylamino)butanoate.

The isomers, N-oxides, and addition salts with a pharmaceutically acceptable acid or base of the preferred compounds are an integral part of the invention.

The present invention relates also to a process for the preparation of compounds of formula (I), characterised in that:

either a 3-amino-2-naphthalenecarboxylic acid compound (II):

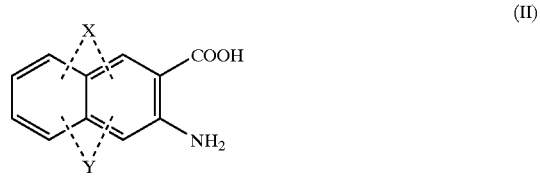

(II)

wherein X and Y are as defined for formula (I), is reacted with a phloroglucinol compound of formula (III):

(III)

wherein R represents a hydrogen atom, a hydroxy group or a linear or branched (C$_1$–C$_6$)alkyl group, to yield the compounds of formula (IV):

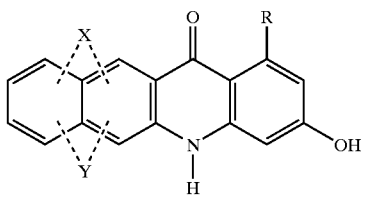

(IV)

wherein X, Y and R are as defined hereinbefore, which are then treated under basic conditions in an aprotic solvent, such as, for example, dimethylformamide, with an alkyne of formula (V):

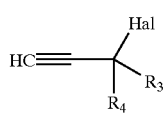

(V)

wherein Hal represents a halogen atom and $R_3$ and $R_4$ are as defined for formula (I), to yield the compounds of formula (VI):

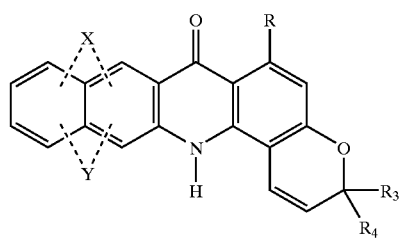

(VI)

wherein X, Y, R, $R_3$ and $R_4$ are as defined hereinbefore, or a 3-halo-2-naphthalenecarboxylic acid compound of formula (VII):

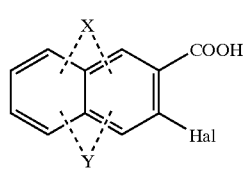

(VII)

wherein X and Y are as defined for formula (I) and Hal represents a halogen atom, such as chlorine or bromine, is reacted with an amino-chromene compound of formula (VIII):

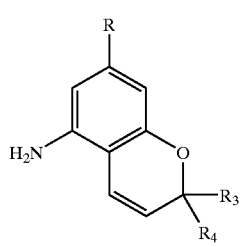

(VIII)

wherein $R_3$ and $R_4$ are as defined for formula (I) and R is as defined hereinbefore, also to yield the compounds of formula (VI):

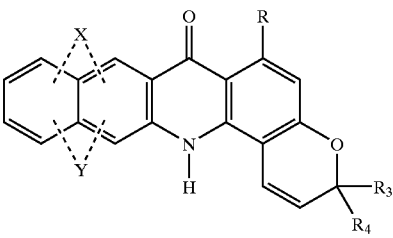

(VI)

wherein X, Y, R, $R_3$ and $R_4$ are as defined hereinbefore, the nitrogen atom of which compounds of formula (VI) is optionally substituted, by the action of an alkyl halide or a dialkyl sulphate in the presence of a deprotonating agent, such as sodium hydride, in an aprotic polar solvent, to yield the compounds of formula (IX):

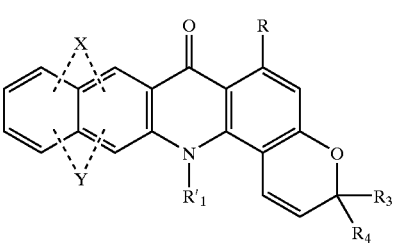

(IX)

wherein X, Y, R, $R_3$ and $R_4$ are as defined hereinbefore, and $R'_1$ represents a linear or branched $(C_1-C_6)$alkyl group, which compounds of formula (IX) are subjected to the action of an alkylating agent, such as a dialkyl sulphate, or of an acylating agent, to yield the compounds of formula (X):

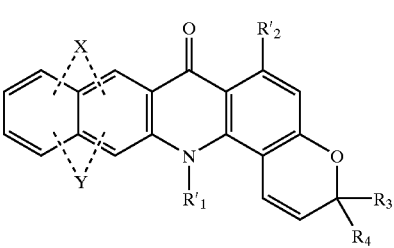

(X)

wherein X, Y, $R'_1$, $R_3$ and $R_4$ are as defined hereinbefore and $R'_2$ represents an alkoxy group (optionally substituted by a group of formula $NR_9R_{10}$ wherein $R_9$ and $R_{10}$ are as defined for formula (I)), or a linear or branched $(C_1-C_6)$alkylcarbonyloxy group, which compound of formula (X), when $R'_2$ represents an alkoxy group for example, is treated with a compound of formula (XI):

HNRaRb (XI)

wherein Ra represents a hydrogen atom, a linear or branched $(C_1-C_6)$alkyl group, an aryl group, or an aryl-($C_1$–$C_6$)alkyl group in which the alkyl moiety is linear or branched, and Rb represents a hydrogen atom, a linear or branched ($C_1$–$C_6$)alkyl group, an aryl group, an aryl-($C_1$–$C_6$)alkyl group in which the alkyl moiety is linear or branched, a group of formula —$R_{11}$—$NR_9R_{10}$ wherein $R_{11}$, $R_{10}$ and $R_9$ are as defined for formula (I), a linear or branched ($C_1$–$C_6$)alkylcarbonyl group in which the alkyl moiety is optionally substituted by a group $NR_7R_8$ as defined for formula (I), a heterocycloalkylene group (the terms "alkylene" and "heterocycle" being as defined for formula (I)) or a group of formula —$R_{11}$—CO—$R_{12}$ wherein $R_{11}$ and $R_{12}$ are as defined for formula (I), to yield the compounds of formula (XII):

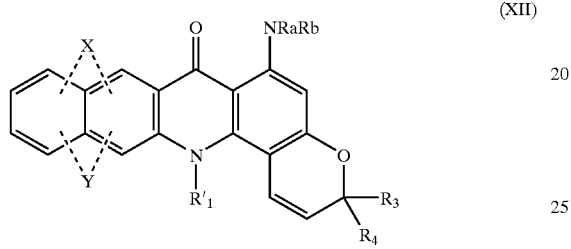

(XII)

wherein X, Y, $R'_1$, $R_3$, $R_4$, Ra and Rb are as defined hereinbefore, the totality of the compounds of formulae (VI), (IX), (X) and (XII) constituting the compounds of formula (XIII):

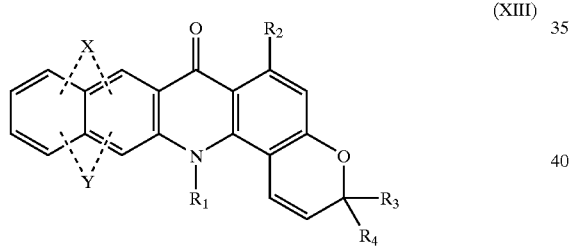

(XIII)

wherein X, Y, $R_1$, $R_2$, $R_3$ and $R_4$ are as defined in the general definition of formula (I), which compounds of formula (XIII) are subjected a) ⇒ either to the action of osmium tetroxide in a polar medium and in the presence of 4-methylmorpholine-N-oxide, to yield the compounds of formulae (XIV/a) and (XIV/b):

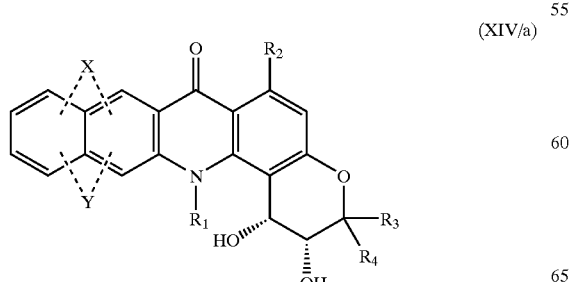

(XIV/a)

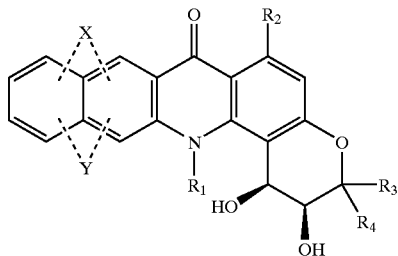

(XIV/b)

wherein X, Y, $R_1$, $R_2$, $R_3$ and $R_4$ are as defined hereinbefore, it also being possible for the compounds of formulae (XIV/a) and (XIVb) to be obtained separately by chiral synthesis and especially by asymmetric cis dihydroxylation starting from compound (XIII) using chiral ligands of the pyridine or phthalazine type bisubstituted by Cinchona alkaloids, such as dihydroquinine and its dextrorotatory diastereoisomer, dihydroquinidine, b) ⇒ or to the action of potassium permanganate in a polar medium, to yield the compounds of formula (XV):

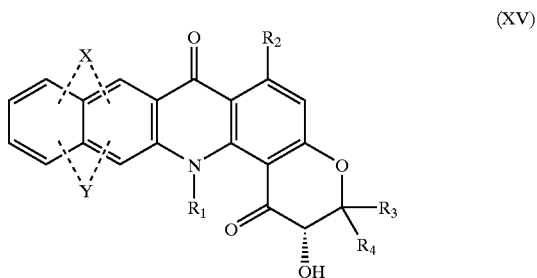

(XV)

wherein X, Y, $R_1$, $R_2$, $R_3$ and $R_4$ are as defined hereinbefore, which compounds of formula (XV) are subjected to reductive conditions in the presence of $NaBH_4$ for example, to yield the compounds of formula (XIV/c):

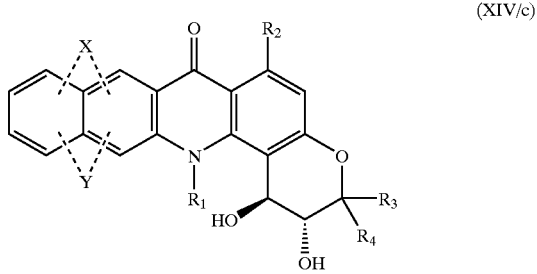

(XIV/c)

wherein X, Y, $R_1$, $R_2$, $R_3$ and $R_4$ are as defined hereinbefore, the totality of the compounds of formulae (XIV/a), (XIV/b) and (XIV/c) constituting the compounds of formula (XIV):

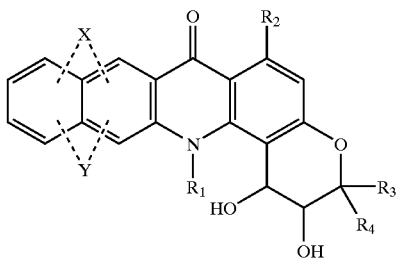

wherein X, Y, $R_1$, $R_2$, $R_3$ and $R_4$ are as defined hereinbefore, which compounds of formula (XIV) are subjected:
either to the action of an alcohol of formula $R_{20}$—OH wherein $R_{20}$ represents a linear or branched ($C_1$–$C_6$)alkyl group, to yield the compounds of formula (XVI/a):

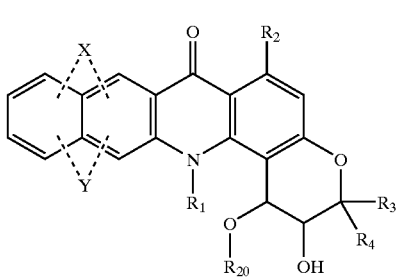

wherein X, Y, $R_1$, $R_2$, $R_3$, $R_4$ and $R_{20}$ are as defined hereinbefore, the alcohol function of which compounds of formula (XVI/a) is esterified in the presence of a compound of formula

wherein U and V are as defined for formula (I) and W represents a leaving group, to yield the compounds of formula (I/a), a particular case of the compounds of formula (I):

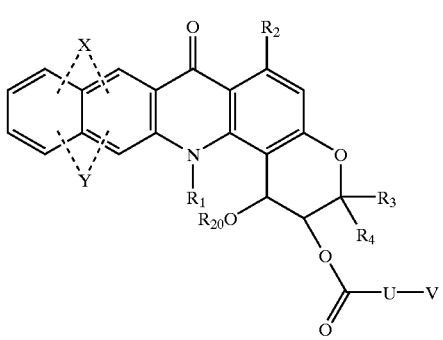

wherein X, Y, $R_1$, $R_2$, $R_3$, $R_4$, $R_{20}$, U and V are as defined hereinbefore, or to the action of an alkyl iodide of formula $R'_{20}$-I wherein $R'_{20}$ represents a linear or branched ($C_1$–$C_6$)alkyl group, in the presence of a silver salt, to yield the compounds of formula (XVI/b):

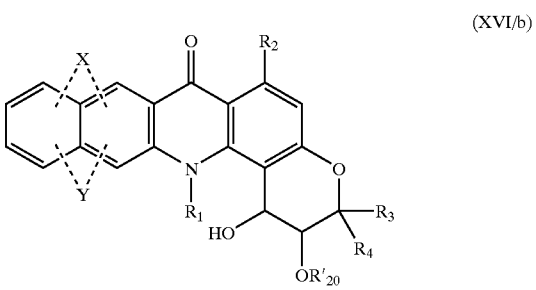

a particular case of the compounds of formula (I), wherein X, Y, $R_1$, $R_2$, $R_3$, $R_4$ and $R'_{20}$ are as defined hereinbefore, the alcohol function of which compounds of formula (XVI/b) is esterified in the presence of a compound of formula

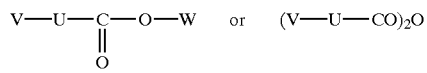

as defined hereinbefore, to yield the compounds of formula (I/b):

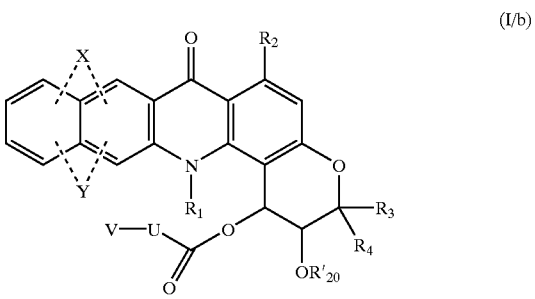

a particular case of the compounds of formula (I), wherein X, Y, $R_1$, $R_2$, $R_3$, $R_4$, $R'_{20}$, U and V are as defined hereinbefore,
or to the direct action of a compound of formula

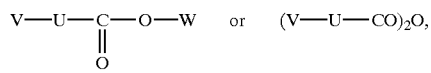

as defined hereinbefore, in the presence of a base, such as triethylamine or 4-dimethylaminopyridine, in order to obtain the compounds of formula (I/c), a particular case of the compounds of formula (I):

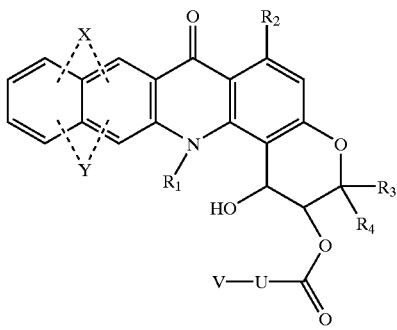

(I/c)

wherein X, Y, $R_1$, $R_2$, $R_3$, $R_4$, U and V are as defined hereinbefore, which compound of formula (I/c) may be subjected again, under the same operating conditions, to the action of an anhydride of formula $(R_{30}CO)_2O$ wherein $R_{30}$ represents a linear or branched $(C_1-C_6)$alkyl group, an aryl group or an aryl-$(C_1-C_6)$alkyl group in which the alkyl moiety is linear or branched, to yield the compounds of formula (I/d):

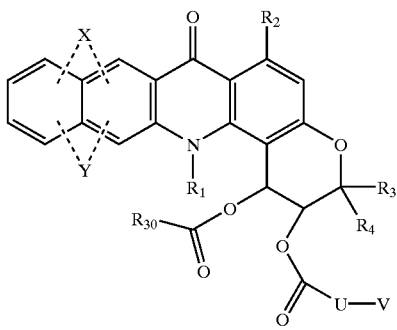

(I/d)

wherein X, Y, $R_1$, $R_2$, $R_3$, $R_4$, $R_{30}$, U and V are as defined hereinbefore, or which compound of formula (I/c) may be treated again with a compound of formula

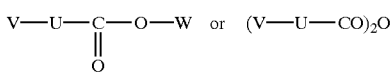

as defined hereinbefore, to yield the compounds of formula (I/e), a particular case of the compounds of formula (I):

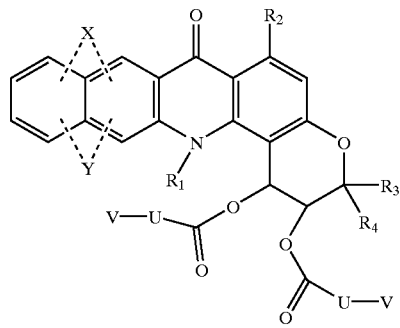

(I/e)

wherein X, Y, $R_1$, $R_2$, $R_3$, $R_4$, U and V are as defined for formula (I), it being understood that the two U groups and the two V groups may each be identical or different, c) ⇨ or to the action of a peracid, such as m-chloroperbenzoic acid, to yield the compound of formula (XVII):

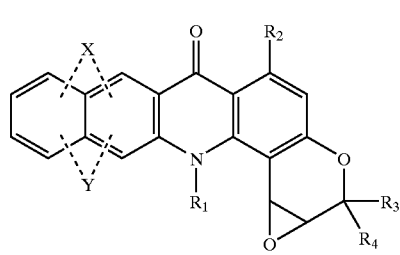

(XVII)

wherein X, Y, $R_1$, $R_2$, $R_3$ and $R_4$ are as defined hereinbefore, which compound of formula (XVII) is optionally treated with ammoniac or a primary or secondary amine to yield the compounds of formula (XVIII/a) and/or (XVIII/b) depending upon the nature of the reagents:

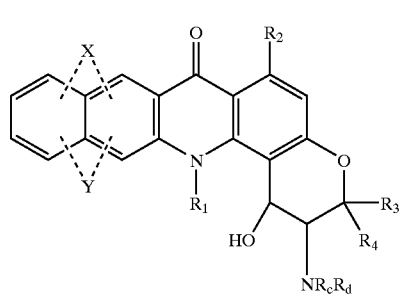

(XVIII/a)

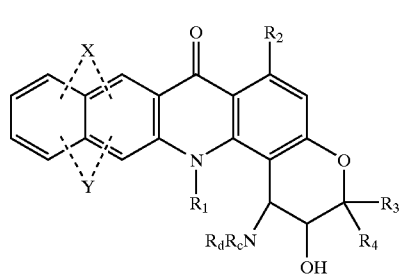

(XVIII/b)

wherein X, Y, $R_1$, $R_2$, $R_3$ and $R_4$ are as defined hereinbefore, and $R_c$ and $R_d$ represent a hydrogen atom or a linear or branched ($C_1$–$C_6$)alkyl group, which compounds of formulae (XVIII/a) and (XVIII/b) are treated with a compound of formula

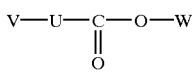

as defined hereinbefore, to yield the compounds of formulae (I/f) and (I/g), respectively, particular cases of the compounds of formula (I):

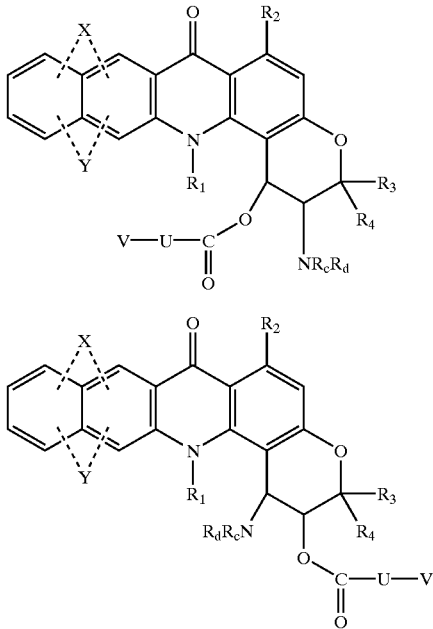

wherein X, Y, $R_1$, $R_2$, $R_3$, $R_4$, $R_c$, $R_d$, U and V are as defined hereinbefore,
which compounds (I/a) to (I/g) constitute the totality of the compounds of the invention, which are purified, if necessary, according to a conventional purification technique, may be separated, if desired, into their various isomers according to a conventional separation technique, and which are converted, if desired, into N-oxides thereof and, where appropriate, into addition salts thereof with a pharmaceutically acceptable acid or base.

The compounds of formulae (II), (III), (V), (VII), (VIII) and (XI) are either commercial compounds or are obtained according to conventional methods of organic synthesis. The compounds of formula (VIII), for example, are obtained according to the conditions described in *Chem. Ber.* 1978, 191, 439. The condensation reaction between the compounds of formula (VII) and the compounds of formula (VIII) is described, for example, in the journal *Heterocycles*, 1992, 34(4), 799–806.

The compounds of formula (I) have especially valuable anti-tumour properties. They have excellent in vitro cytotoxicity on cell lines from murine and human tumours because of specific blocking of the cell cycle, and they have in vivo activity, in mice, on murine and human transplantable tumours. The characteristic properties of those compounds enables them to be used therapeutically as anti-tumour agents.

The present invention relates also to pharmaceutical compositions comprising as active ingredient at least one compound of formula (I), its optical isomers, N-oxides or an addition salt thereof with a pharmaceutically acceptable acid or base, alone or in combination with one or more inert, non-toxic, pharmaceutically acceptable excipients or carriers.

Among the pharmaceutical compositions according to the invention, special mention is made of those that are suitable for oral, parenteral (intravenous, intramuscular or subcutaneous), per- or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, eye or nose drops, etc.

The useful dosage varies according to the age and weight of the patient, the route of administration, the nature and severity of the disorder and whether any associated treatments are being taken, and ranges from 0.5 mg to 500 mg in one or more administrations per day.

The following Examples illustrate the invention but do not limit it in any way.

The starting materials used are known products or are prepared according to known procedures.

The structures of the compounds described in the Examples and Preparations were determined according to the usual spectrophotometric techniques (infrared, nuclear magnetic resonance, etc.).

PREPARATION A (±)-cis-1,2-Dihydroxy-6-methoxy-3,3,14-trimethyl-2,3,7,14-tetrahydro-1H-benzo[b]pyrano[3,2-h]acridin-7-one Step A
1,3-Dihydroxy-5,12-dihydro-benzo[b]acridin-12-one 3.5 g of 1,3,5-trihydroxybenzene and 62.5 mg of para-toluenesulphonic acid are added to a solution of 5 g of 3-amino-2-naphthalenecarboxylic acid in 50 ml of heptan-1-ol. The mixture is stirred for 48 hours at reflux using a Dean Stark apparatus, and then the reaction mixture is concentrated in vacuo. The residue is chromatographed over silica gel (eluant: cyclohexane/acetone: 90/10). The isolated product is crystallised from a cyclohexane/acetone mixture and yields 5.2 g of the expected product.

Step B
6-Hydroxy-3,3-dimethyl-7,14-dihydro-3H-benzo[b]pyrano[3,2-h]acridin-7-one 2 g of anhydrous potassium carbonate are added, under an inert atmosphere, to a solution of 2 g of the product of Step A in 50 ml of anhydrous dimethylformamide. After stirring for 15 minutes at 65° C., 2.4 g of anhydrous potassium iodide and 4.4 g of 3-chloro-3-methyl-1-butyne are added and the reaction mixture is maintained at 65° C. for 24 hours and then at 130° C. for 1 hour 30 minutes. After cooling, the solution is hydrolysed and then extracted with dichloromethane. The combined organic phases are washed with water and then with a 1M potassium hydroxide solution, dried over sodium sulphate and then evaporated. Chromatography over silica gel (cyclohexane/acetone: 90/10) yields 1.10 g of the expected product.

Melting point: 225° C.

Step C
6-Methoxy-3,3,14-trimethyl-7,14-hydro-3H-benzo[b]pyrano[3,2-h]acridin-7-one 0.16 g of sodium hydride and then, after 15 minutes, 0.65 ml of dimethyl sulphate (6 equivalents) are slowly added at 0° C. under an inert atmosphere to a solution of 0.5 g of product of Step B in 20 ml of anhydrous dimethylformamide. After 1 hour, the reaction mixture is hydrolysed with ice and then extracted with ethyl acetate. After washing the organic phase with an aqueous sodium hydroxide solution, the organic phase is dried over sodium sulphate and then evaporated in vacuo. Chromatography over silica gel (cyclohexane/acetone: 98/2) enables isolation of 0.42 g of the expected product.

Melting point: 188° C.

Step D
(±)-cis-1,2-Dihydroxy-6-methoxy-3,3,14-trimethyl-2,3,7,14-tetrahydro-1H-benzo[b]pyrano[3,2-h]acridin-7-one 3.8 ml of a solution at 2.5% of osmium tetroxide in 2-methyl-2-propanol is added to a solution of 2 g of the product of Step C and 0.9 g of 4-methylmorpholine-N-oxide monohydrate in 40 ml of a tert-butanol/tetrahydrofuran/water mixture (10/3/1). After 2 days at room temperature, 105 ml of a saturated NaHSO$_3$ solution are added and the reaction mixture is stirred for 1 hour and then extracted with dichloromethane. The combined organic phases are dried over sodium sulphate and concentrated in vacuo. Chromatography over silica gel (dichloromethane/methanol: 95/5) enables isolation of 1.3 g of the expected product.

Melting point: 194° C.

PREPARATION B (±)-cis-1,2-Dihydroxy-6-(dimethylaminoethylamino)-3,3,14-trimethyl-2,3,7,14-tetrahydro-1H-benzo[b]pyrano[3,2-h]acridin-7-one Step A
6-(Dimethylaminoethylamino)-3,3,14-trimethyl-7,14-dihydro-3H-benzo[b]pyrano[3,2-h]acridin-7-one 4 ml of N,N-dimethylethylenediamine are added to 0.15 g of the product obtained in Step C of Preparation A. After 5 days' reaction at 70° C. under an inert atmosphere, the reaction mixture is evaporated under reduced pressure. The resulting residue is chromatographed over silica gel (cyclohexane/ethyl acetate: 80/20) enabling isolation of the expected product.

Melting point: oil

Mass spectrum: (DIC/NH$_3$): m/z: 428 (M+H)$^+$

Step B
(±)-cis-1,2-Dihydroxy-6-(dimethylaminoethylamino)-3,3,14-trimethyl-2,3,7,14-tetrahydro-1H-benzo[b]pyrano[3,2-h]acridin-7-one The procedure is as for Step D of Preparation A using the product obtained in the preceding Step as substrate.

PREPARATION C (±)-cis-1,2-Dihydroxy-6-(diethylaminopropylamino)-3,3,14-trimethyl-2,3,7,14-tetrahydro-1H-benzo[b]pyrano[3,2-h]acridin-7-one The procedure is as for Preparation B, Steps A and B, using N,N-diethylpropyldiamine as reagent in Step A.

PREPARATION D cis-6-[(2-Morpholin-4-yl)ethylamino]-1,2-dihydroxy-3,3,14-trimethyl-2,3,7,14-tetrahydro-1H-benzo[b]pyrano[3,2-h]acridin-7-one The procedure is as for Preparation B, Steps A and B, using 4-(2-aminoethyl)morpholine as reagent in Step A.

PREPARATION E cis-10,11-Dichloro-1,2-dihydroxy-6-methoxy-3,3,14-trimethyl-2,3,7,14-tetrahydro-1H-benzo[b]pyrano[3,2-h]acridin-7-one The procedure is as for Preparation A, Steps A to D, using 3-amino-6,7-dichloro-2-naphthalenecarboxylic acid as substrate in Step A.

PREPARATION F cis-1,2-Dihydroxy-6,9,12-trimethoxy-3,3,14-trimethyl-2,3,7,14-tetrahydro-1H-benzo[b]pyrano[3,2-h]acridin-7-one The procedure is as for Preparation A, Steps A to D, using 3-amino-5,8-dimethoxy-2-naphthalenecarboxylic acid as substrate in Step A.

Preparation G cis-1,2-Dihydroxy-6-methoxy-3,3-dimethyl-2,3,7,14-tetrahydro-1H-benzo[b]pyrano[3,2-h]acridin-7-one Step A
3-[(7-Methoxy-2,2-dimethyl-2H-chromen-5-yl)amino]-2-naphthoic acid A mixture of 1.2 mmol of 5-amino-6-methoxy-2,2-dimethylchromene, 1.2 mmol of 2-bromo-3-benzoic acid, 0.327 g of potassium acetate, and 12 mg of copper acetate is suspended in 8 ml of 2-propanol and 0.25 ml of triethylamine and then heated at reflux for 24 hours. The reaction mixture is then concentrated under reduced pressure, taken up in a CH$_2$Cl$_2$/1N HCl mixture, extracted with dichloromethane, dried and evaporated. Chromatography of the residue over silica gel (cyclohexane/ethyl acetate: 1/1) enables isolation of the expected product.

Mass spectrum (DIC/NH$_3$): 376 [M+H]$^+$

Step B
6-Methoxy-3,3-dimethyl-3,14-dihydro-7H-benzo[b]pyrano[3,2-h]acridin-7-one 1.02 mmol of the compound obtained in Step A in 14 ml of dichloromethane is treated with 1 ml of trifluoroacetic acid. After 2 hours at room temperature, the reaction mixture is evaporated. The residue is taken up in a mixture of dichloromethane and a saturated NaHCO$_3$ solution, extracted with dichloromethane, washed with a 10% sodium hydroxide solution and then extracted again with dichloromethane. After conventional treatment, chromatography of the residue over silica gel (dichloromethane/methanol: 98/2) enables isolation of the expected product.

Mass spectrum E.I: m/z: 357 (M$^+$); 342 (M−15)$^{+.}$

Step C
cis-1,2-Dihydroxy-6-methoxy-3,3-dimethyl-2,3,7,14-tetrahydro-1H-benzo[b]pyrano[3,2-h]acridin-7-one A mixture of 0.279 mmol of the compound obtained in Step B, a 2.5% solution of osmium tetroxide in 3.8 ml of 2-methyl-2-propanol and 60 mg 4-methylmorpholine N-oxide is dissolved in 5 ml of a 10/3/1 mixture of tert-BuOH/tetrahydrofuran/H$_2$O. After stirring for 24 hours at room temperature, 5 ml of a saturated NaHSO$_3$ solution is added. After stirring for 1 hour, the reaction mixture is extracted with dichloromethane. The organic phase is subsequently dried and then concentrated under reduced pressure. Chromatography of the residue over silica gel (dichloromethane/methanol: 97/3) enables isolation of the expected product.

Mass spectrum (DIC/NH$_3$): 392 [M+H]$^{+\cdot}$

EXAMPLE 1

(±)-cis-4-{[1-(Acetyloxy)-6-methoxy-3,3,14-trimethyl-7-oxo-2,3,7,14-tetrahydro-1H-benzo[b]pyrano[3,2-h]acridin-2-yl]oxy}-4-oxobutanoic acid 5 equivalents of succinic anhydride and 1 mg of dimethylaminopyridine are added to a solution of 0.74 mmol of the compound of Preparation A in 7 ml of anhydrous pyridine. After stirring for 17 hours at room temperature and in darkness, 25 ml of acetic anhydride are added. The reaction mixture is cooled to −15° C. and stirring is maintained for 1 hour 30 minutes. The reaction mixture is then concentrated under reduced pressure. Chromatography over silica gel (dichloromethane/methanol) enables isolation of the expected product.

Mass spectrum: (FAB): m/z=548 [M+H]$^+$

Melting point: 154° C.

EXAMPLE 2

(±)-cis-4-{[1-(Acetyloxy)-6-}[2-(dimethylamino)ethyl]amino}-3,3,14-trimethyl-7-oxo-2,3,7,14-tetrahydro-1H-benzo[b]pyrano[3,2-h]acridin-2-yl)oxy]-4-oxobutanoic acid The procedure is as for Example 1 using the compound of Preparation B as substrate.

EXAMPLE 3

(±)-cis-5-{[1-(Acetyloxy)-6-methoxy-3,3,14-trimethyl-7-oxo-2,3,7,14-tetrahydro-1H-benzo[b]pyrano[3,2-h]acridin-2-yl]oxy}-5-oxopentanoic acid The procedure is as for Example 1 using glutaric anhydride as reagent instead of succinic anhydride.

Mass spectrum: (DIC/NH$_3$): m/z=562 [M+H]$^+$

Melting point: 155° C.

EXAMPLE 4

(±)-cis-1-(Acetyloxy)-6-methoxy-3,3,14-trimethyl-7-oxo-2,3,7,14-tetrahydro-1H-benzo[b]pyrano[3,2-h]acridin-2-yl 2,3-dihydroxypropanoate Step A
(±)-cis-1-(Acetyloxy)-6-methoxy-3,3,14-trimethyl-7-oxo-2,3,7,14-tetrahydro-1H-benzo[b]pyrano[3,2-h]acridin-2-yl acrylate 0.6 mmol of acryloyl chloride is added to a solution of 0.5 mmol of the compound of Preparation A in 3 ml of anhydrous pyridine. After stirring for 2.5 days at room temperature and in darkness, 2 ml of acetic anhydride are added and stirring is maintained for 48 hours. The reaction mixture is then concentrated under reduced pressure. Chromatography over silica gel (dichloromethane) enables isolation of the expected product.

Mass spectrum: (DIC/NH$_3$): m/z=502 [M+H]$^+$

Step B
(±)-cis-1-(Acetyloxy)-6-methoxy-3,3,14-trimethyl-7-oxo-2,3,7,14-tetrahydro-1H-benzo[b]pyrano[3,2-h]acridin-2-yl 2,3-dihydroxypropanoate 1 ml of 2.5% osmium tetroxide solution in tert-butanol and 4.4 mmol of 4-methylmorpholine-N-oxide monohydrate are added to a suspension of 0.4 mmol of the compound obtained in Step A in 5 ml of a tert-butanol/tetrahydrofuran/water mixture (10/3/1 volume to volume). After 2 days' stirring at room temperature, 50 ml of an aqueous saturated NaHCO$_3$ solution are added. After stirring for 1 hour, extraction with dichloromethane and concentration under reduced pressure, chromatography over silica gel (dichloromethane/methanol: 96/4) enables isolation of the expected product.

Mass spectrum: (DIC/NH$_3$): m/z=536 [M+H]$^{+\cdot}$

EXAMPLE 5

(±)-cis-1-(Acetyloxy)-6-methoxy-3,3,14-trimethyl-7-oxo-2,3,7,14-tetrahydro-1H-benzo[b]pyrano[3,2-h]acridin-2-yl 2-[(tert-butoxycarbonyl)amino]acetate 0.6 mmol of dicyclohexylcarbodiimide is slowly added to a solution, cooled to 0° C., of 0.5 mmol of the compound of Preparation A and 0.5 mmol of 2-[(tert-butoxycarbonyl)amino]acetic acid in 10 ml of dimethylformamide. The reaction mixture is maintained at 0° C. for 5 hours and at room temperature for 16 hours. After filtration and evaporation under reduced pressure, the residue is dissolved in 2 ml of anhydrous pyridine, 2 ml of acetic anhydride are added, and the mixture is stirred at room temperature and in darkness for 48 hours. After concentration of the reaction mixture under reduced pressure, chromatography of the residue over silica gel (dichloromethane) enables isolation of the expected product.

Mass spectrum: (DIC/NH$_3$): m/z=605 [M+H]$^{+\cdot}$

EXAMPLE 6

(±)-cis-1-(Acetyloxy)-6-methoxy-3,3,14-trimethyl-7-oxo-2,3,7,14-tetrahydro-1H-benzo[b]pyrano[3,2-h]acridin-2-yl 2-aminoacetate 0.14 μl of iodotrimethylsilane is added at room temperature to a solution of 0.1 mmol of the compound of Example 5 in 1 ml of chloroform. The reaction mixture is stirred for 5 minutes at room temperature and then evaporated to dryness under reduced pressure. Chromatography over silica gel (dichloromethane/methanol: 85/15) enables isolation of the expected product.

Mass spectrum: (DIC/NH$_3$): m/z=505 [M+H]$^{+\cdot}$

Example 7

(±)-cis-4-({1-[(3-Carboxypropanoyl)oxy]-6-methoxy-3,3,14-trimethyl-7-oxo-2,3,7,14-tetrahydro-1H-benzo[b]pyrano[3,2-h]acridin-2-yl}oxy)-4-oxobutanoic acid The product is isolated in the course of chromatography of the compound of Example 1.

Mass spectrum (FAB): m/z: 606 [M+H]+
Melting point: 128° C.

EXAMPLE 8 cis-4-{[1-(Acetyloxy)-10,11-dichloro-6-methoxy-3, 3,14-trimethyl-7-oxo-2,3,7,14-tetrahydro-1H-benzo [b]pyrano[3,2-h]acridin-2-yl]oxy}-4-oxobutanoic acid The procedure is as for Example 1 using the compound of Preparation E as substrate.

EXAMPLE 9 cis-4-{[1-(Acetyloxy)-6,9,12-trimethoxy-3,3,14-trimethyl-7-oxo-2,3,7,14-tetrahydro-1H-benzo[b] pyrano[3,2-h]acridin-2-yl]oxy}-4-oxobutanoic acid The procedure is as for Example 1 using the compound of Preparation F as substrate.

EXAMPLE 10 cis-4-[(1-(Acetyloxy)-6-{[3-(diethylamino)propyl] amino}-3,3,14-trimethyl-7-oxo-2,3,7,14-tetrahydro-1H-benzo[b]pyrano[3,2-h]acridin-2-yl)oxy]-4-oxobutanoic acid The procedure is as for Example 1 using the compound of Preparation C as substrate.

EXAMPLE 11 cis-4-[(1-(Acetyloxy)-3,3,14-trimethyl-6-{[2-(4-morpholinyl)ethyl]amino}-7-oxo-2,3,7,14-tetrahydro-1H-benzo[b]pyrano[3,2-h]acridin-2-yl) oxy]-4-oxobutanoic acid The procedure is as for Example 1 using the compound of Preparation D as substrate.

EXAMPLE 12 cis-4-{[6-Methoxy-3,3,14-trimethyl-7-oxo-1-(propionyloxy)-2,3,7,14-tetrahydro-1H-benzo[b] pyrano[3,2-h]acridin-2-yl]oxy}-4-oxobutanoic acid The procedure is as for Example 1 using propionic anhydride as reagent instead of acetic anhydride.

EXAMPLE 13 cis-4-{[1-(Isobutyryloxy)-6-methoxy-3,3,14-trimethyl-7-oxo-2,3,7,14-tetrahydro-1H-benzo[b] pyrano[3,2-h]acridin-2-yl]oxy}-4-oxobutanoic acid The procedure is as for Example 1 using isobutyric anhydride as reagent instead of acetic anhydride.

EXAMPLE 14 cis-4-{[1-(Benzoyloxy)-6-methoxy-3,3,14-trimethyl-7-oxo-2,3,7,14-tetrahydro-1H-benzo[b]pyrano[3,2-h] acridin-2-yl]oxy}-4-oxobutanoic acid The procedure is as for Example 1 using benzoic anhydride as reagent instead of acetic anhydride.

EXAMPLE 15 cis-4-{[6-Methoxy-3,3,14-trimethyl-7-oxo-1-(pentanoyloxy)-2,3,7,14-tetrahydro-1H-benzo[b] pyrano[3,2-h]acridin-2-yl]oxy}-4-oxobutanoic acid The procedure is as for Example 1 using valeric anhydride as reagent instead of acetic anhydride.

EXAMPLE 16 cis-[1-(Acetyloxy)-6-methoxy-3,3,14-trimethyl-7-oxo-2,3,7,14-tetrahydro-1H-benzo[b]pyrano[3,2-h] acridin-2-yl](dimethylamino)acetate 300 mg of the compound of Preparation A is dissolved in 4 ml of anhydrous dimethylformamide at 0° C. 90 mg of 4-dimethylaminopyridine and 152 mg of N,N-dimethylglycine are added to the mixture. After a pause of 5 minutes at 0° C., 142 mg of 1-(3-dimethylaminopropyl)-3-ethylcarbodiimide hydrochloride are added. The reaction mixture is stirred for 4 hours and then 2 ml of ice-cold water are added. The mixture is extracted with dichloromethane. The organic solutions are combined, dried over anhydrous sodium sulphate, filtered and then distilled under reduced pressure. The resulting residue is chromatographed over silica gel ($CH_2Cl$/MeOH: 85/15) to yield the expected product.

Mass spectrum (DIC/$NH_3$): 533 [M+H]+.

EXAMPLE 17 cis-[1-(Acetyloxy)-6-methoxy-3,3,14-trimethyl-7-oxo-2,3,7,14-tetrahydro-1H-benzo[b]pyrano[3,2-h] acridin-2-yl]4-(dimethylamino)butanoate The procedure is as for Example 16 using 4-dimethylaminobutyric acid as reagent instead of N,N-dimethylglycine.

EXAMPLE 18 cis-[1-(Acetyloxy)-6-methoxy-3,3,14-trimethyl-7-oxo-2,3,7,14-tetrahydro-1H-benzo[b]pyrano[3,2-h] acridin-2-yl](acetylamino)acetate The procedure is as for Example 16 using N-acetylglycine as reagent instead of N,N-dimethylglycine.

Mass spectrum (DIC/$NH_3$): 547 [M+H]+.

EXAMPLE 19 cis-4-{[1-(Acetyloxy)-6-methoxy-3,3-dimethyl-7-oxo-2,3,7,14-tetrahydro-1H-benzo[b]pyrano[3,2-h] acridin-2-yl]oxy}-4-oxobutanoic acid The procedure is as for Example 1 using the compound of Preparation G as substrate.

EXAMPLE 20

Lysine salt of (±)-cis-4-{[1-(acetyloxy)-6-methoxy-3,3,14-trimethyl-7-oxo-2,3,7,14-tetrahydro-1H-benzo[b]pyrano[3,2-h]acridin-2-yl]oxy}-4-oxobutanoic acid 0.1 g of the compound of Example 1 is dissolved in 20 ml of ethanol in the presence of one equivalent of lysine hydrate. The solution is stirred for 30 minutes and then evaporated and concentrated under reduced pressure enabling isolation of the expected product in the form of a salt.

EXAMPLE 21

Lysine salt of (±)-cis-4-({1-[(3-carboxypropanoyl) oxy]-6-methoxy-3,3,14-trimethyl-7-oxo-2,3,7,14-tetrahydro-1H-benzo[b]pyrano[3,2-h]acridin-2-yl}oxy)-4-oxobutanoic acid The procedure is as for Example 20 using the compound of Example 7 as substrate and 2 equivalents of lysine.

EXAMPLE 22 cis-5-({1-[(4-Carboxybutanoyl)oxy]6-methoxy-3,3,
14-trimethyl-7-oxo-2,3,7,14-tetrahydro-1H-benzo[b]
pyrano[3,2-h]acridin-2-yl}oxy)-5-oxopentanoic acid The product is isolated in the course of chromatography of the compound of Example 3.

Mass spectrum (DIC/NH$_3$): 634 [M+H]$^+$

Melting point: 118° C.

EXAMPLE 23 cis-5-{[1-(Acetyloxy)-6-methoxy-3,3,14-trimethyl-
7-oxo-2,3,7,14-tetrahydro-1H-benzo[b]pyrano[3,2-h]
acridin-2-yl]oxy} 2,4-dimethyl-5-oxopentanoic acid The procedure is as for Example 1 using 2,4-dimethylglutaric acid as reagent instead of succinic anhydride.

EXAMPLE 24 cis-5-{[1-(Acetyloxy)-6-methoxy-3,3,14-trimethyl-
7-oxo-2,3,7,14-tetrahydro-1H-benzo[b]pyrano[3,2-h]
acridin-2-yl]oxy} 3-hydroxy-3-methyl-5-
oxopentanoic acid The procedure is as for Example 1 using 3-hydroxy-3-methylglutaric acid as reagent instead of succinic anhydride.

EXAMPLE 25 cis-1-(Acetyloxy)-6-methoxy-3,3,14-trimethyl-7-
oxo-2,3,7,14-tetrahydro-1H-benzo[b]pyrano[3,2-h]
acridin-2-yl 5-(benzylamino)-5-oxopentanoate The procedure is as for Example 1 using benzylglutaramic acid as reagent instead of succinic anhydride.

EXAMPLE 26 cis-1-(Acetyloxy)-6-methoxy-3,3,14-trimethyl-7-
oxo-2,3,7,14-tetrahydro-1H-benzo[b]pyrano[3,2-h]
acridin-2-yl 5-(4-methoxyphenyl)-5-oxopentanoate The procedure is as for Example 1 using 5-(4-methoxyphenyl)-5-oxovaleric acid as reagent instead of succinic anhydride.

PHARMACOLOGICAL STUDY OF THE COMPOUNDS OF THE INVENTION

EXAMPLE 27

In vitro Activity

The murine leukaemia L1210 and the human colon carcinoma HT-29 were used in vitro. The cells are cultured in complete RPMI 1640 culture medium containing 10% foetal calf serum, 2 mM glutamine, 50 U/ml of penicillin, 50 µg/ml of streptomycin and 10 mM Hepes, pH: 7.4. The cells are distributed in microplates and exposed to the cytotoxic compounds for 4 doubling periods, that is to say 48 hours (L1210) or 96 hours (HT-29). The number of viable cells is then quantified by a colorimetric assay, the Microculture Tetrazolium Assay (J. Carmichael et al., *Cancer Res.*, 47, 936–942, (1987)). The results are expressed as IC$_{50}$ values, which is the cytotoxic concentration that inhibits the proliferation of the treated cells by 50%.

By way of Example, the compounds of Examples 1 and 7 exhibit an IC$_{50}$ of 2 µM and 2.3 µM, respectively, thus demonstrating their activity to be greater than that of the reference compound acronycine.

EXAMPLE 28

In vivo Activity

1-Anti-tumour Activity on the Leukaemia P 388

The line P 388 (murine leukaemia) was supplied by the National Cancer Institute (Frederick, USA). The tumour cells (10$^6$ cells) were inoculated on day 0 into the peritoneal cavity of female B6D2F1 mice (Iffa Credo, France). Six mice weighing from 18 to 20 g were used per experimental group. The compounds were administered by the intraperitoneal route on day 1.

The anti-tumour activity is expressed as % of T/C:

$$T/C \text{ \% (survival)} = \frac{\text{Median survival time of the treated animals}}{\text{Median survival time of the control animals}} \times 100$$

The compounds of the invention are very active in this model, whilst acronycine is only marginally active, and induce T/C>150% at doses of less than 100 mg/kg.

2-Anti-tumour Activity on the Colon Adenocarcinoma C38

The tumour fragments of colon adenocarcinoma C38, weighing about 30 mg, were implanted on day 0 below the skin of B6D2F1 mice (Iffa Credo, France).

After growth of the tumour, the mice were divided into control groups (18 animals) and treated groups (6 to 7 animals), the groups being homogeneous in respect of the tumour size. The compounds were administered i.v. once per week for 3 weeks (on days 10, 17 and 24), at their maximum tolerated dose (MTD), MTD/2 and MTD/4.

The tumours were measured twice per week and the volume of the tumours was calculated according to the formula: Volume (mm$^3$)=length (mm)×width (mm$^2$)/2. The anti-tumour activity is expressed as a % of T/C:

$$\% T/C = \frac{\text{median } Vt/V0 \text{ of the treated animals}}{\text{median } Vt/V0 \text{ of the control animals}} \times 100$$

V0 and Vt being the initial volume of the tumour and its volume at the time of measurement t, respectively.

The optimum dose is the dose that yields the lowest T/C without toxicity (premature death or weight loss of more than 20%).

The compounds of the invention have proved to be more active, in this model, than the reference compound which is acronycine, so demonstrating their strong therapeutic potential.

EXAMPLE 29

Pharmaceutical Composition: Injectable Solution

Compound of Example 1 10 mg
Distilled water for injectable preparations 25 ml

What is claimed is:

1. A compound selected from those of formula (I):

(I)

wherein:

X and Y, which may be identical or different, each independently of the other represents a group selected from hydrogen, halogen, hydroxy, mercapto, cyano, nitro, linear or branched ($C_1$–$C_6$)alkyl, linear or branched ($C_1$–$C_6$)alkoxy, trihalo-($C_1$–$C_6$)alkyl in which alkyl is linear or branched, and amino (optionally substituted by one or two, identical or different, linear or branched ($C_1$–$C_6$)alkyl which may themselves be substituted by linear or branched ($C_1$–$C_6$)alkoxy or by a group of formula —$NR_7R_8$ wherein $R_7$ and $R_8$, which may be, identical or different, each independently of the other represents hydrogen, linear or branched ($C_1$–$C_6$)alkyl, aryl or aryl-($C_1$–$C_6$)alkyl in which alkyl is linear or branched), or X and Y together form methylenedioxy, or ethylenedioxy, it being understood that X and Y may be present on one or the other of the two adjacent benzene rings, $R_1$ represents hydrogen, or linear or branched ($C_1$–$C_6$) alkyl, $R_2$ represents:
hydrogen,
hydroxy,
linear or branched ($C_1$–$C_6$)alkyl,
linear or branched ($C_1$–$C_6$)alkoxy optionally substituted by group selected from:
group of formula $NR_9R_{10}$ wherein $R_9$ and $R_{10}$, which may be, identical or different, each independently of the other represents hydrogen, linear or branched ($C_1$–$C_6$)alkyl, or linear or branched ($C_1$–$C_6$)hydroxyalkyl, and
linear or branched ($C_1$–$C_6$)alkylcarbonyloxy, or
amino optionally substituted by:
one or two, identical or different, linear or branched ($C_1$–$C_6$)alkyl, aryl, or aryl-($C_1$–$C_6$)alkyl in which alkyl is linear or branched,
linear or branched ($C_1$–$C_6$)alkylcarbonyl optionally substituted by —$NR_7R_8$ wherein $R_7$ and $R_8$ are as defined hereinbefore,
group of formula —$R_{11}$—$NR_9R_{10}$, wherein $R_{11}$ represents linear or branched ($C_1$–$C_6$)alkylene, and $R_9$ and $R_{10}$, which may be identical or different, each independently of the other represents hydrogen, linear or branched ($C_1$–$C_6$)alkyl group, or linear or branched ($C_1$–$C_6$)hydroxyalkyl,
linear or branched ($C_1$–$C_6$)alkylene, substituted by saturated or unsaturated, monocyclic or bicyclic heterocycle having from 5 to 7 ring members containing one or two hetero atoms selected from oxygen, nitrogen, and sulphur, or
by group of formula —$R_{11}$—CO—$R_{12}$ wherein $R_{11}$ is as defined hereinbefore, and $R_{12}$ represents hydroxy, or linear or branched ($C_1$–$C_6$)alkoxy, $R_3$ and $R_4$, which may be identical or different, each independently of the other represents hydrogen, or linear or branched ($C_1$–$C_6$)alkyl, $R_5$ and/or $R_6$ represent(s) group of formula —O—CO—U—V wherein:
U represents linear or branched ($C_1$–$C_8$)alkylene, optionally substituted by one or more, identical or different, groups selected from aryl, hydroxy, and linear or branched ($C_1$–$C_6$)alkoxy,
V represents group selected from:
carboxy,
—$CO_2R_{13}$ wherein $R_{13}$ represents linear or branched ($C_1$–$C_6$)alkyl (optionally substituted by one or more hydroxy), aryl, or aryl-($C_1$–$C_6$)alkyl in which alkyl is linear or branched,
hydroxy,
linear or branched ($C_1$–$C_6$)alkoxy,
—$NR_7R_8$ wherein $R_7$ and $R_8$, which may be, identical or different, are as defined hereinbefore,
—$NR_7$—$CO_2R_{13}$ wherein $R_7$ and $R_{13}$ are as defined hereinbefore,
—$NR_7$—$COR_{13}$ wherein $R_7$ and $R_{13}$ are as defined hereinbefore,
—$COR_{13}$ wherein $R_{13}$ is as defined hereinbefore, and
—CO—$NR_7R_8$ wherein $R_7$ and $R_8$, which may be identical or different, are as defined hereinbefore,
and when only one of the two groups $R_5$ and $R_6$ represents group of formula —O—CO—U—V, then the other of the said $R_5$ and $R_6$ groups represents group Z selected from:
hydroxy,
linear or branched ($C_1$–$C_6$)alkoxy,
linear or branched ($C_1$–$C_6$)alkylcarbonyloxy,
arylcarbonyloxy,
aryl-($C_1$–$C_6$)alkylcarbonyloxy in which alkyl is linear or branched, and
amino optionally substituted by one or two, identical or different, linear or branched ($C_1$–$C_6$)alkyl, their isomers, N-oxides, and pharmaceutically-acceptable acid or base addition salts thereof, it being understood that "Aryl" mean phenyl or naphtyl, optionally containing one or more, identical or different, substituent selected from hydroxy, halogen, carboxy, nitro, amino, ($C_1$–$C_6$) alkylamino, di($C_1$–$C_6$)alkylamino in which each alkyl is linear or branched, linear or branched ($C_1$–$C_6$)alkoxy, linear or branched ($C_1$–$C_6$)aryl, and linear or branched ($C_1$–$C_6$) alkylcarbonyloxy.

2. A compound of claim 1 wherein $R_3$ and $R_4$, which may be identical or different, represent linear or branched ($C_1$–$C_6$)alkyl, their isomers, N-oxides, and pharmaceutically-acceptable acid or base addition salts thereof.

3. A compound of claim 1, wherein $R_3$ and $R_4$, which are identical, each represents methyl, their isomers, N-oxides, and pharmaceutically-acceptable acid or base addition salts thereof.

4. A compound of claim 1, wherein $R_2$ represents linear or branched ($C_1$–$C_6$)alkoxy, or optionally substituted amino as defined for formula (I), their isomers, N-oxides, and pharmaceutically-acceptable acid or base addition salts thereof.

5. A compound of claim 1, wherein $R_5$ represents —O—CO—U—V wherein U and V are as defined for formula (I) and 1% represents Z as defined for formula (I), their isomers, N-oxides, and pharmaceutically-acceptable acid or base addition salts thereof.

6. A compound of claim 1, wherein $R_6$ and $R_5$, which are identical, each represents —O—CO—U—V wherein U and V are as defined for formula (I), their isomers, N-oxides, and pharmaceutically-acceptable acid or base addition salts thereof.

7. A compound of claim 1, wherein $R_5$ represents —O—CO—U—V wherein U represents linear $(C_1-C_4)$ alkylene and V represents a group selected from carboxy, —$NR_7R_8$, —$NR_7$—$CO_2R_{13}$, and —$NR_7$—$COR_{13}$ wherein $R_7$, $R_8$ and $R_{13}$, which may be, identical or different, represent hydrogen, or linear or branched $(C_1-C_6)$alkyl, their isomers, N-oxides, and pharmaceutically-acceptable acid or base addition salts thereof.

8. A compound of claim 1, wherein $R_6$ represents linear or branched $(C_1-C_6)$alkylcarbonyloxy, their isomers, N-oxides, and pharmaceutically-acceptable acid or base addition salts thereof.

9. Compounds of claim 1 which are:

(±)-cis-4-{[1-(acetyloxy)-6-methoxy-3,3,14-trimethyl-7-oxo-2,3,7,14-tetrahydro-1H-benzo[b]pyrano[3,2-h]acridin-2-yl]oxy}-4-oxobutanoic acid, (±)-cis-4-({1-[(3-carboxypropanoyl)oxy]-6-methoxy-3,3,14-trimethyl-7-oxo-2,3,7,14-tetrahydro-1H-benzo[b]pyrano[3,2-h]acridin-2-yl}oxy)-4-oxobutanoic acid, (±)-cis-5-{[1-(acetyloxy)-6-methoxy-3,3,14-trimethyl-7-oxo-2,3,7,14-tetrahydro-1H-benzo[b]pyrano[3,2-h]acridin-2-yl]oxy}-5-oxopentanoic acid, cis-[1-(acetyloxy)-6-methoxy-3,3,14-trimethyl-7-oxo-2,3,7,14-tetrahydro-1H-benzo[b]pyrano[3,2-h]acridin-2-yl](dimethylamino)acetate, and cis-[1-(acetyloxy)-6-methoxy-3,3,14-trimethyl-7-oxo-2,3,7,14-tetrahydro-1H-benzo[b]pyrano [3,2-h]acridin-2-yl]4-(dimethylamino)butanoate, their isomers, N-oxides, and pharmaceutically-acceptable acid or base addition salts thereof.

10. A method for treating a living body afflicted with a cancer susceptible to treatment with acronycine comprising the step of administering to the living body in need thereof an amount of a compound of claim 1, which is effective for alleviation of said cancer.

11. A pharmaceutical composition comprising a compound as claimed in claim 1, together with one or more pharmaceutically-acceptable excipients or vehicles.

12. A compound of claim 1 which is (±)-cis-5-{1[1-(acetyloxy)-6-methoxy-3,3,14-trimethyl-7-oxo-2,3,7,14-tetrahydro-1h-benzo[b]pyrano[3,2-h]acridin-2-yl]oxy}-5-oxopentanoic acid.

* * * * *

UNITED STATES PATENT AND TRADEMARK OFFICE
CERTIFICATE OF CORRECTION

PATENT NO.    : 6,503,919 B1
DATED         : January 7, 2003
INVENTOR(S)   : Michel Koch et al.

It is certified that error appears in the above-identified patent and that said Letters Patent is hereby corrected as shown below:

Title page,
Item [73], Assignee, "Les Laboratoires Server" should read -- Les Laboratoires Servier --.

Column 25,
Line 6, "1%" should read -- $R_6$ --.

Column 26,
Line 27, "1h" should read -- 1H --.

Signed and Sealed this

Third Day of June, 2003

JAMES E. ROGAN
*Director of the United States Patent and Trademark Office*